United States Patent [19]
Scarrow

[11] Patent Number: 5,531,733
[45] Date of Patent: Jul. 2, 1996

[54] HANGER STRAP

[75] Inventor: David Scarrow, Avon, United Kingdom

[73] Assignee: Rexam Medical Packaging Limited, United Kingdom

[21] Appl. No.: 280,589

[22] Filed: Jul. 26, 1994

[30] Foreign Application Priority Data

Jul. 26, 1993 [GB] United Kingdom ............... 9315427

[51] Int. Cl.⁶ ............................. A61B 19/00; A47H 1/10; B65D 33/14
[52] U.S. Cl. ...................... 604/411; 24/16 PB; 248/322; 383/22
[58] Field of Search ............................ 604/403, 411, 604/416, 905; 248/317, 322, 74.3, 225.2; 24/16 PB, 30.5 P; 215/228, 306; 220/375, 212.5; 383/22, 25, 13

[56] References Cited

U.S. PATENT DOCUMENTS 3,257,694  3/1963  Litwin ................... 24/16 PB
3,397,430  6/1967  Pearl ..................... 24/16 PB
4,526,576  7/1985  Cianci ..................... 604/322
5,308,347  5/1994  Sunago et al. ............. 604/403

FOREIGN PATENT DOCUMENTS 1239955  5/1967  Germany.

Primary Examiner—Mary Beth Jones
Assistant Examiner—David J. Cho
Attorney, Agent, or Firm—Larson and Taylor

[57] ABSTRACT

A hanger strap has a connection portion which, in use, is connected to a component, particularly part of a medical fluid administration kit, which provides a narrow-mouthed slot. An elongate strap body extends from the connection portion and has a wide portion, a narrow portion and a hanging means (usually a loop). For storage, the strap lies flat against the component. For use, the strap is bent up and its narrow portion is passed into the slot through the mouth. The strap is pulled through the slot until the wide portion is therein. This cannot escape through the mouth, and formations (e.g. ratchet teeth) resist its withdrawal.

9 Claims, 5 Drawing Sheets

HANGER STRAP

BACKGROUND OF THE INVENTION

The present invention relates to a hanger strap, and to an article including such a strap (either as an integral part or as a connectable component). It is particularly concerned with the field of medical products, especially products that have to be produced and packaged in a sterile form, such as components used in the administration of medical fluids (such as blood, blood components and drugs for intravenous administration).

It is known (for example from EP-A-0,285,424) to provide apparatus for administering a voluminous liquid component in which a second component (usually solid) is dissolved. The apparatus includes a flexible container of liquid, and a cup which is coupled, or can be coupled, to the container. A tubular spike extends through the base of the cup into the interior. It is communicable with the interior of the flexible container. In use, a vial containing the solid component is pushed onto the spike, so that liquid from the container can enter the vial and be returned to the container, which thus contains a solution of the solid. It is normally then desired for the assembly to be suspended, with the cup and vial above the container, so that the solution can be dispensed from the container in a downward direction. EP-A-0,285,424 is concerned with systems in which the vial is trapped in the cup (once it has been penetrated by the spike) by a further cup-like component which is inverted, and forms a sealed enclosure with the cup. This component can provide, on its base, an aperture by which the assembly can be suspended. However, we have now developed systems in which there is no need for the additional cup. Therefore there is a problem as to how the assembly can be conveniently suspended. It is, of course, very important that the various components should be packaged and stored hygienically. As one part of this, it is desirable for the cup member to have its mouth sealed by a diaphragm which is peeled away immediately prior to the use. Therefore the peripheral end face of the cup wall cannot conveniently carry hanger means. Since such products would also generally be over-wrapped, it is also very desirable that all components should pack neatly and not occupy large amounts of space.

SUMMARY OF THE INVENTION

In one aspect, the present invention provides a hangable assembly comprising a component having a body and an upper flange portion having a narrow-mouthed slot; and an elongate hanger strap having a flexible strap body terminating at one end in an enlargement providing a hanging formation (preferably a loop) and being connected or connectable at the other end to the component body; the intermediate strap body portion having a narrow region relatively close to the hanging formation and a wider region remoter from the hanging formation; the arrangement being such that, with the strap connected to the component body so as to extend downwardly, it can be bent upwardly, and the narrow region can then be passed through the mouth of the narrow-mouthed slot, and the strap can be pulled upwardly, remaining within the slot, until the wider region is within the slot. The dimensions of the wider region are such as to resist escape from the slot. Preferably it comprises formations which engage formations associated with the slot so as to tend to retain the strap in the upwardly-pulled configuration. Thus the strap body may broaden gradually so that there is a wedging effect in the slot and/or there may be engagement formations such as projections which are deformable to pass through the slot and then snap-engage above it. There may be two sets of projections.

The hanger strap may be formed separately from the component and they may have mutual engagement formations. Thus the body may have means defining a downwardly-open channel, and an end region of the strap may be arranged to engage in this. This may rely on friction and/or bonding and/or there may be positive engagement formations, such as resilient projections engaging behind projections or in recesses provided by the component body.

The component may comprise a cup member of a medical administration apparatus as outlined above. Thus it may have a cup body with an upper flange in which is provided the narrow-mouthed slot. The flange may be covered by a membrane prior to use. Removal of the membrane for use may also uncover the slot. The cup body may have a downwardly open channel, in which an end of a hanging strap is engaged. This engagement may be effected by the manufacturer.

In another aspect, the invention provides a hanger strap for use in a hangable assembly. The invention is not restricted to medical fluid dispensing systems, but may be used for other types of apparatus, particularly those for medical environments. An example is a disposable container for 'sharps'.

DESCRIPTION OF THE PREFERRED EMBODIMENTS

Figure 1:
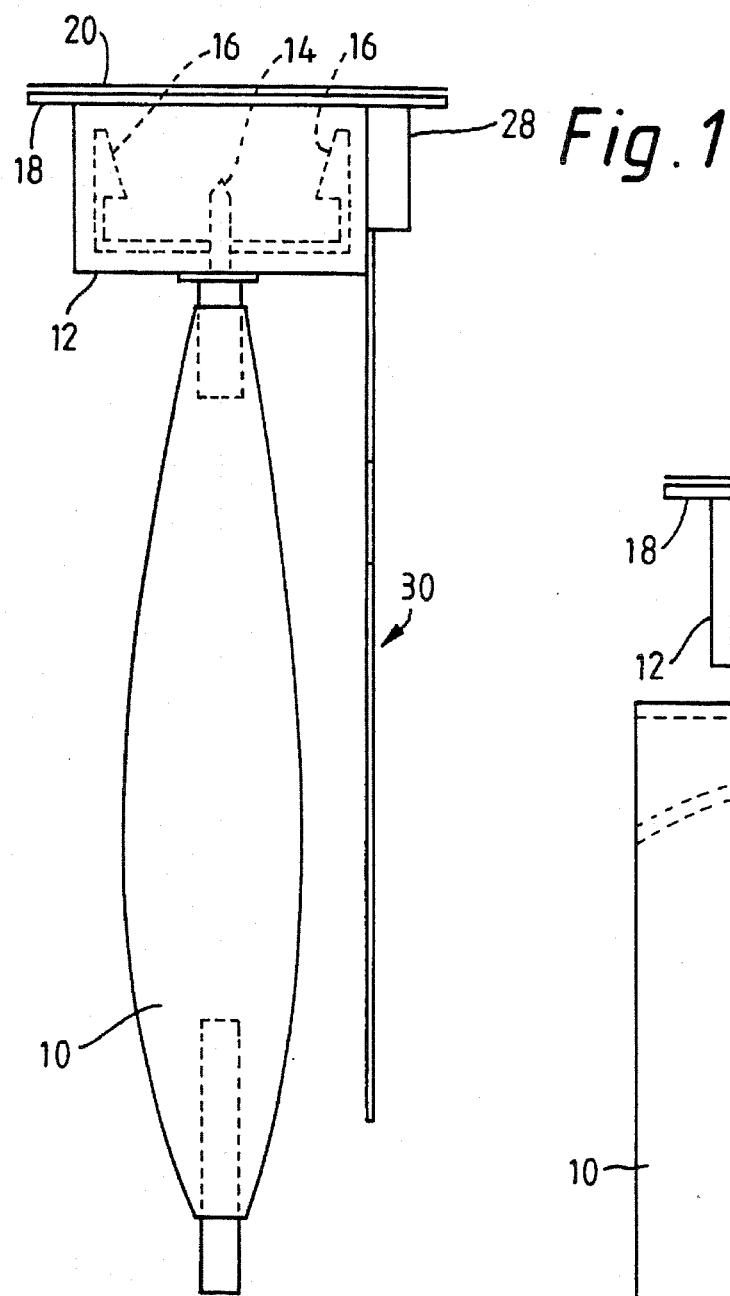
FIG. 1 is a side elevation of medical fluid administration assembly embodying the present invention.
Figure 2:
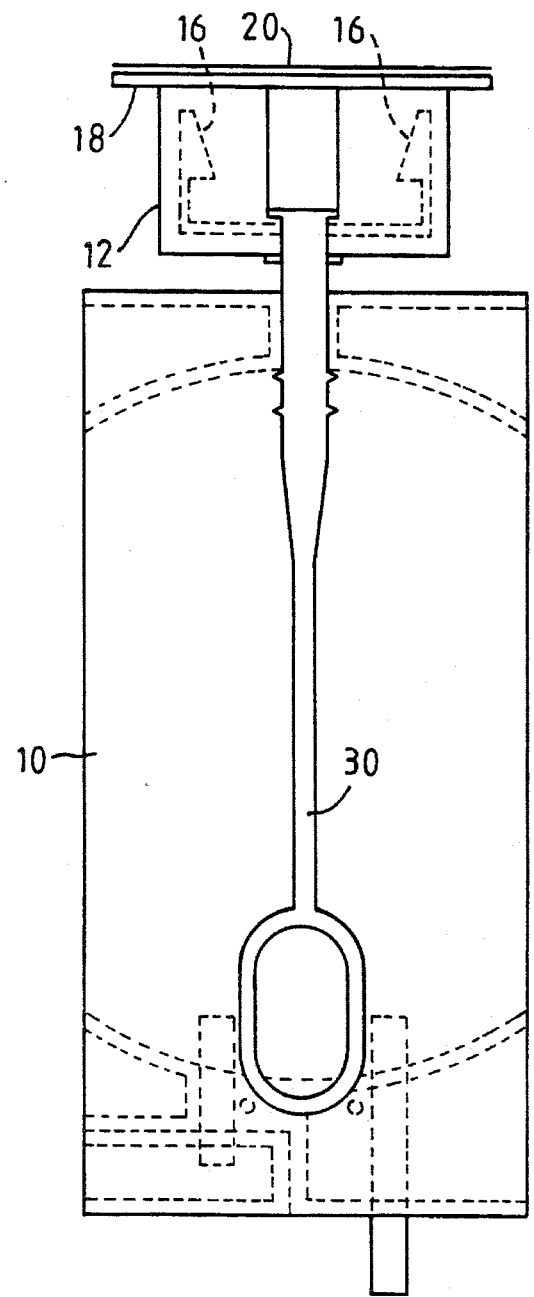
FIG. 2 is a front elevation of medical fluid administration assembly embodying the present invention.
Figure 3:
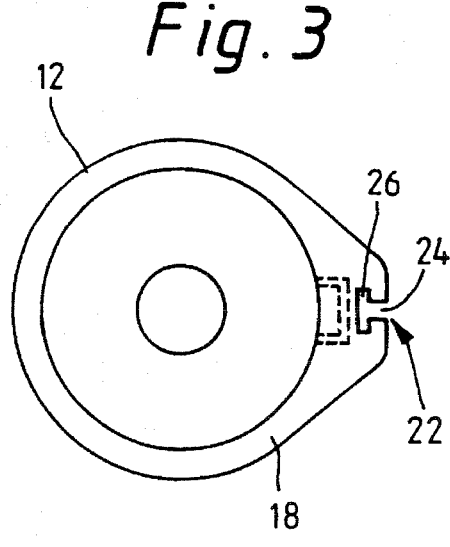
FIG. 3 is a top plan view of the cup shown in FIGS. 1 and 2.
Figure 4:
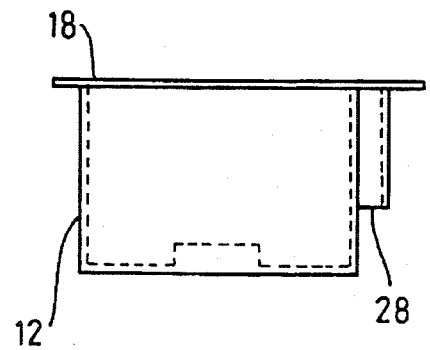
FIG. 4 is a side elevation of the cup.
Figure 5A:
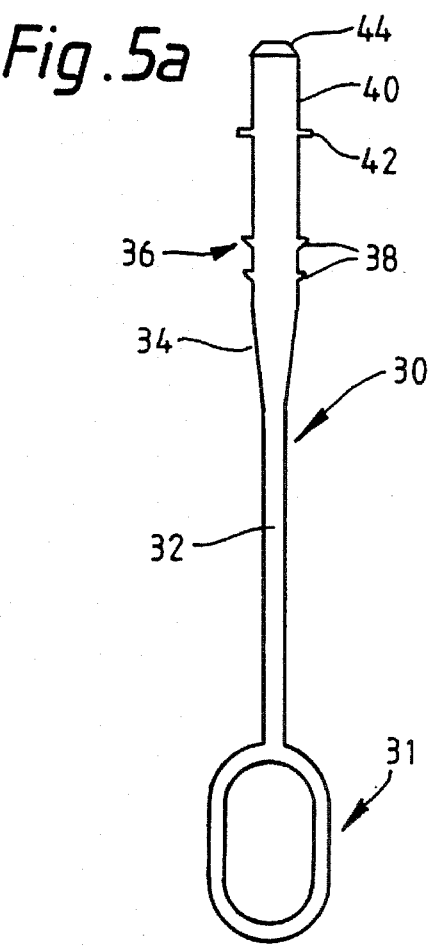
FIGS. 5a and b are front and side elevations of a hanger strap.
Figure 5B:
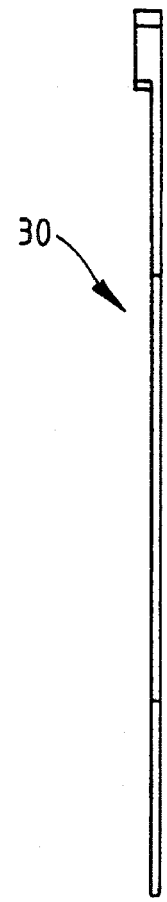

FIGS. 1 and 2 show a container 10 of medical fluid coupled at an upper end to a cup member 12. A tubular spike 14 extends through the base of the cup into the cup interior, and is communicable with the interior of the fluid container 10. Within the cup there is a crown-like array of detent arms 16. At the top of the cup, there is an outwardly-directed flange 18. This is closed by a peelable seal 20. In a conventional system, the flange 18 would be circular, extending beyond the cup wall by a constant amount. However, in this embodiment, at one side it extends to a greater extent, and its furthest-projecting portion is pierced by a through-opening in the form of a narrow-mouthed slot 22 (see FIG. 3), having a narrow mouth 24 leading to a flat slot portion 26. Beneath this part of the flange, the body of the cup 12 is provided with a downwardly-open tubular portion 28. A hanger strap 30 has one end engaged therein. As can be seen from FIGS. 5 and 6, the hanger strap is an elongate component. It is suitably formed of a flexible plastic material, e.g. polypropylene. Its lower end has a hanger loop 31. ('Upper' and 'lower' refer to the storage configuration shown in FIG. 1.) The lower part of the hanger body 32 is narrow. There is a region of widening 34 leading to an enlarged region 36 having two pairs of closely spaced projections 38. The strap is mostly flat and thin but, adjacent the upper end, there is a thicker plug portion 40, bounded at the lower portion by projections 42 and at the upper end by a tapered portion 44. This is to facilitate its insertion into the channel 28, to produce a wedging or interference fit, with the projection 42 abutting the mouth of the channel 28. As can be seen in FIGS. 1 and 2, when the hanger 30 is engaged in the channel, it extends downwardly and lies over the body of the fluid container 10, and thus does not add to the effective bulk of the assembly.

Figure 6A:
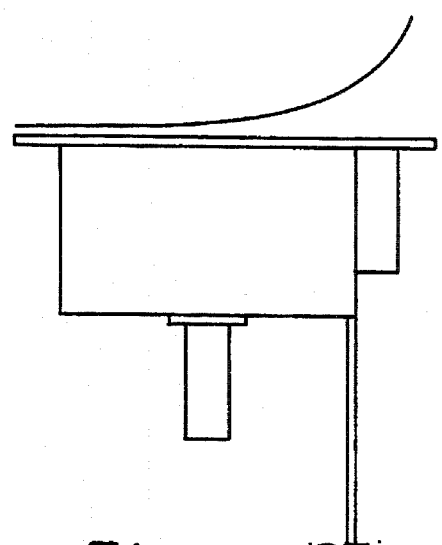
FIG. 6a is a view of a partial operation of the illustrated apparatus.
Figure 6B:
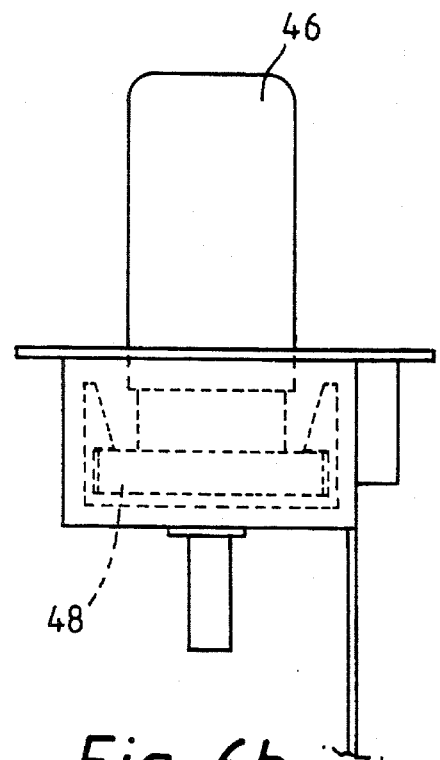
FIG. 6b is a view of a partial operation of the illustrated apparatus.
Figure 6C:
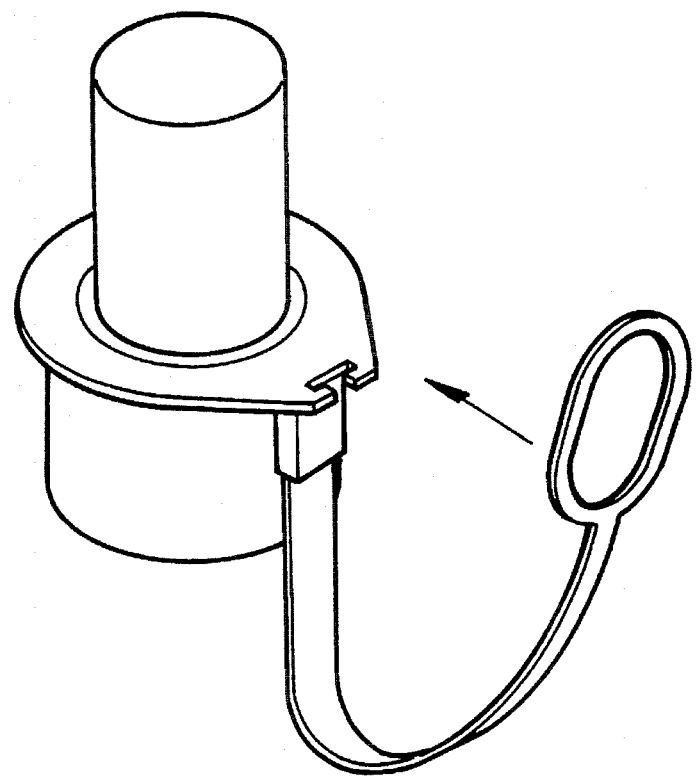
FIG. 6c is a view of a partial operation of the illustrated apparatus.
Figure 6D:
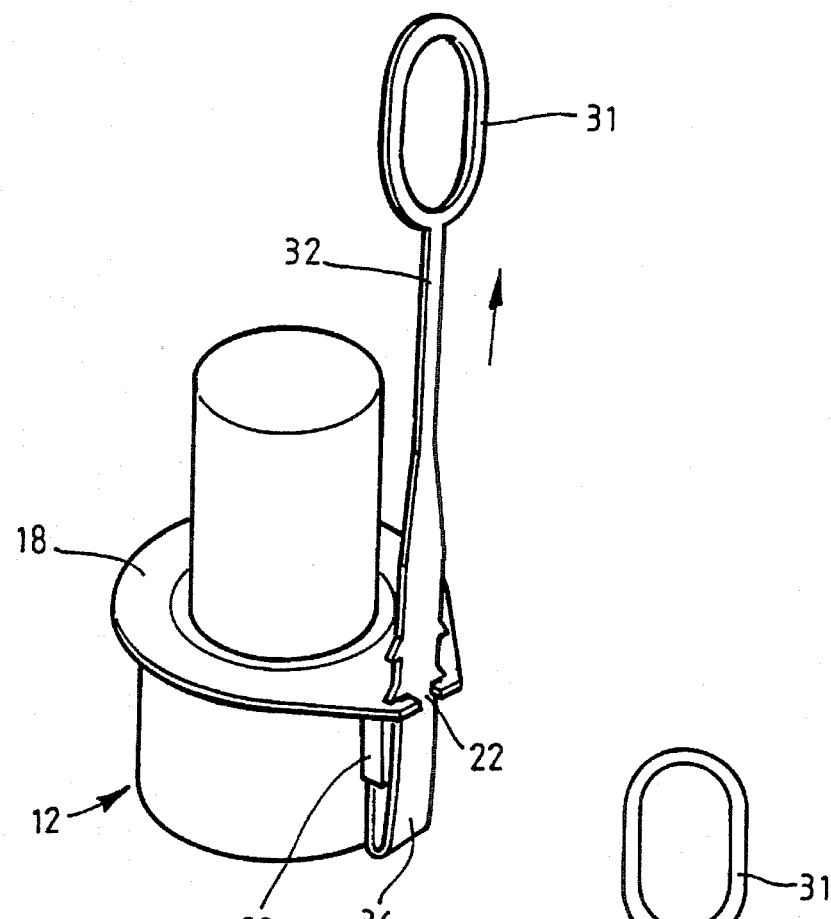
FIG. 6d is a view of a partial operation of the illustrated apparatus.
Figure 7:
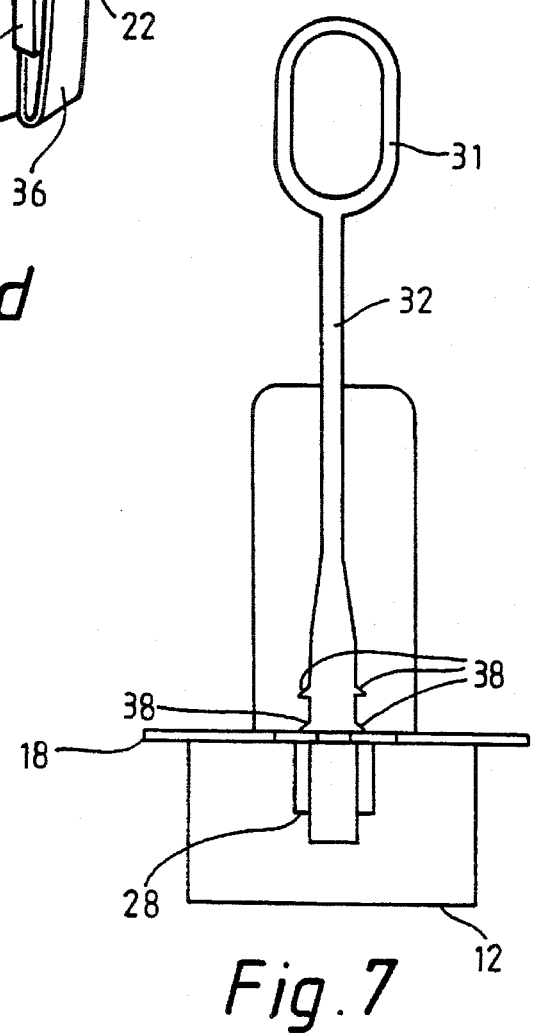
FIG. 7 is a view of the arrangement shown in FIG. 6d as viewed in the direction of arrow Y.

When it is desired to use the assembly, the first step is to peel off the lid 20, as shown in FIG. 6a. A vial 46 is then engaged, by pushing its head end into the cup. The standard vial 46 has an enlarged head 48 which locks behind the detent heads on the resilient arms 16. It has a rubber septum, which is penetrated by the spike 14 as engagement occurs. Then, as shown in FIG. 6c the strap body is bent upwardly. The narrow region 32 of the strap body can easily be passed through the mouth 24 of the slot 22. The strap is further pulled upwardly (using the loop 31), so that the wider parts of the strap body extend through the slot, resisting its withdrawal. Pulling is continued until, as can be seen in FIG. 7, at least one pair of projections 38 is pulled through the slot. This effectively locks the strap in the use configuration. The hanger loop 31 thus projects upwardly, above the vial, but is held quite close to the vial, so that the assembly can be hung stably and in a substantially upright configuration.

Figure 8:
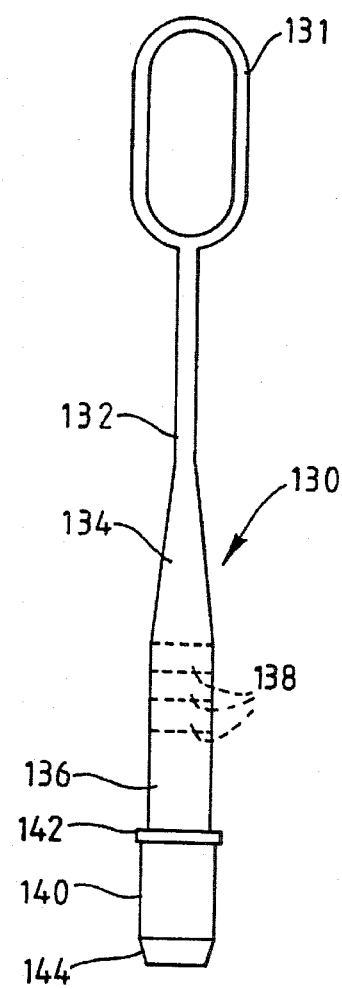
FIG. 8 is a front elevation of a hangar strap of a second embodiment.
Figure 9:
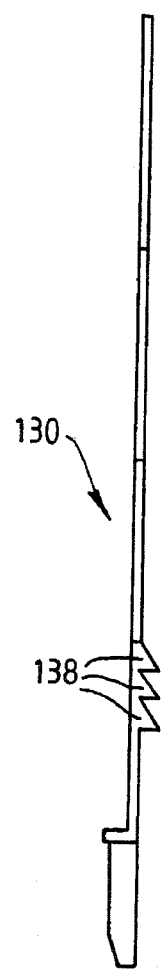
FIG. 9 is a side elevation of a hangar strap of a second embodiment.
Figure 10:
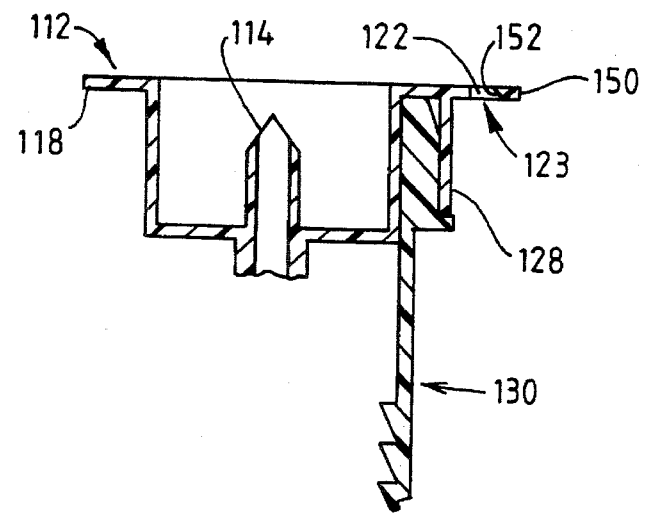
FIG. 10 is a sectional view of part of the second embodiment.

FIGS. 8–10 show a second embodiment. In most respects it is similar to the first and corresponding elements are marked by corresponding reference numerals raised by 100. Thus the hanger strap 130 has a plug portion 140 connected via a flat strip to a hanger loop 131. The strip has a narrow portion 132 adjacent the loop, widening gradually in an intermediate region 134 to a wide portion 136. The wide portion has engagement formations. However, whereas in the first embodiment these are lateral projections 38, in the second embodiment they are ratchet teeth 138 projecting from one face of the strip. The teeth each have a sloping face on the side of the loops 131 and an abrupt face on the side of the plug portion 140.

The cup member 112 may be almost identical to that of the first embodiment. It has a flange with a narrow-mouthed slot whose mouth is wider than (or not substantially narrower than) the narrow portion 132 of the strip, but substantially narrower than the wide portion 136. The body portion 123 of the slot is wide enough to accommodate the wide portion 136 of the strip. As shown in FIG. 10, the flange portions 150 defining the outer edge portions of the slot body 123 have tapered inner surfaces 152, to assist the passage of the ratchet teeth 138. The spacing of the teeth 138 from the plug portion 140 is such that the strap can be engaged in the slot 122 and pulled until all of the teeth 138 are through, by which time there is little or no slack left in the strap beneath the flange, and the resilience of the material tends to pull the strap back.

While the invention has been illustrated above by reference to preferred embodiments, it will be understood by those skilled in the art that various changes may be made without departing from the spirit and scope of the invention. It is intended to cover all such changes and modifications by the appended claims.

I claim:

1. A hangable assembly comprising a component having a body with a web portion defining a narrow-mouth slot; and an elongate hanger strap having a connection portion at one end connected to the component, hanging means at the other end and a flexible strap body connecting the connection portion to the hanger means, said strap body having a narrow portion adjacent the hanger means and a wider portion remote from the hanger means, the wider portion being accommodated within the narrow-mouthed slot but not readily passable through the narrow-mouthed slot, the narrow portion being readily passable through the narrow-mouthed slot.

2. An assembly according to claim 1 wherein the strap body includes engagement formations on a portion thereof such that if the narrow portion is passed into the narrow-mouthed slot and the strap body is then displaced relative to the slot so that the wider portion extends through the slot, the engagement formations engage the web portion to resist withdrawal.

3. An assembly according to claim 2 wherein the engagement formations comprise a tapered region of the strap for wedging in the slot.

4. An assembly according to claim 2 wherein the engagement formations comprise projections on the strap body.

5. As assembly according to claim 4 wherein the projections have a shape for allowing pulling the portion of the strap body bearing the projections through the slot in a direction with the hanging means leading, and for resisting pulling the portion in an opposite direction through the slot.

6. An assembly according to claim 5 wherein the projections comprise ratchet teeth projecting from one face of the strap body.

7. An assembly according to claim 1 wherein the connection portion of the hanger strap comprises plug means and the component body includes complementary socket means for receiving the plug means.

8. An assembly according to claim 1 wherein the component comprises a cup member of a medical administration apparatus, said cup member having a base, a tubular spike extending through the base, a cylindrical cup wall rising from the base, and a peripheral flange extending outwardly from an upper region of the cup wall, said flange including the web portion.

9. An assembly according to claim 8 wherein the strap body is connected to the cup wall beneath the web portion and extends downwardly away from the flange until forcibly bent upwardly against its own resilience.

* * * * *